(12) United States Patent
Kulidjian (10) Patent No.: US 11,819,423 B2
(45) Date of Patent: Nov. 21, 2023

(54) SYSTEMS AND METHODS FOR SELECTING ARTIFICIAL FEMORAL COMPONENTS

(71) Applicant: X40, Inc, La Jolla, CA (US)

(72) Inventor: Anna Andranik Kulidjian, La Jolla, CA (US)

(73) Assignee: X40, Inc., La Jolla, CA (US)

( * ) Notice: Subject to any disclaimer, the term of this patent is extended or adjusted under 35 U.S.C. 154(b) by 514 days.

(21) Appl. No.: 16/856,776

(22) Filed: Apr. 23, 2020

(65) Prior Publication Data
US 2020/0375759 A1    Dec. 3, 2020

Related U.S. Application Data

(63) Continuation-in-part of application No. 16/392,282, filed on Apr. 23, 2019, now Pat. No. 11,129,732.

(51) Int. Cl.
*A61F 2/46* (2006.01)
*A61B 17/15* (2006.01)

(52) U.S. Cl.
CPC ............ *A61F 2/461* (2013.01); *A61B 17/155* (2013.01); *A61F 2002/4658* (2013.01)

(58) Field of Classification Search
CPC ............................... A61F 2/3859; A61F 2/461
See application file for complete search history.

(56) References Cited

U.S. PATENT DOCUMENTS

| | | | |
|---|---|---|---|
| 4,566,466 A | 1/1986 | Ripple et al. | |
| 4,567,885 A | 2/1986 | Androphy | |
| 4,759,350 A | 7/1988 | Dunn et al. | |
| 5,306,285 A | 4/1994 | Miller et al. | |
| 5,462,549 A | 10/1995 | Glock | |
| 5,613,969 A | 3/1997 | Jenkins, Jr. | |
| 5,776,137 A | 7/1998 | Katz | |
| 5,925,049 A | 7/1999 | Gustilo et al. | |
| 6,458,135 B1 * | 10/2002 | Harwin ................ | A61F 2/4657 606/88 |
| 6,875,222 B2 | 4/2005 | Long et al. | |
| 7,744,616 B2 | 6/2010 | O'Donoghue | |
| 7,789,885 B2 | 9/2010 | Metzger | |
| 8,323,288 B2 | 12/2012 | Zajac | |
| 8,545,506 B2 | 10/2013 | Long et al. | |

(Continued)

OTHER PUBLICATIONS

International Search Report dated Aug. 11, 2020, in International Application No. PCT/US20/29565, filed Apr. 23, 2020; 3 pages.

*Primary Examiner* — Sameh R Boles
(74) *Attorney, Agent, or Firm* — Jason Jones (57) ABSTRACT

A system for preparing a femur to receive an implant includes a saw blade positionable in a first saw blade slot of a distal cutting block and operable to form an axial cut surface on the patient's femur. The saw blade carries on a first side thereof nominal A/P sizing indicia that increments negatively from an anterior top of concavity of the medial condyle to a posterior top of concavity of the medial condyle, when the saw blade is positioned on the axial cut surface of the patient's femur. The saw blade also carries nominal M/L sizing indicia on a second, opposing side of the saw blade. An A/P chamfer cutting block is positionable on the axial cut surface of the femur and is coupled to at least one rotational guide that rotationally orients the A/P chamfer cutting block relative to the patient's femur.

11 Claims, 8 Drawing Sheets

(56) References Cited

U.S. PATENT DOCUMENTS

| | | |
|---|---|---|
| 8,828,020 B2 | 9/2014 | Dower et al. |
| 8,882,776 B2 | 11/2014 | Long et al. |
| 9,668,746 B2 | 6/2017 | Lee et al. |
| 9,848,896 B2 | 12/2017 | Emslie et al. |
| 9,974,547 B2 | 5/2018 | Lin et al. |
| 2003/0045883 A1 | 3/2003 | Chow et al. |
| 2004/0129125 A1 | 7/2004 | Colquhoun |
| 2004/0153066 A1 | 8/2004 | Coon et al. |
| 2006/0111726 A1 | 5/2006 | Felt et al. |
| 2010/0057089 A1 | 3/2010 | Axelson, Jr. |
| 2010/0063508 A1 | 3/2010 | Borja et al. |
| 2011/0130762 A1 | 6/2011 | Metzger et al. |
| 2014/0018813 A1 | 1/2014 | Mckinnon et al. |
| 2014/0088598 A1 | 3/2014 | Bonutti |
| 2014/0249534 A1 | 9/2014 | Bertram, III |
| 2016/0256178 A1 | 9/2016 | Tuttle et al. |
| 2017/0128079 A1 | 5/2017 | Brown |
| 2018/0185097 A1 | 7/2018 | Langhorn et al. |
| 2018/0228614 A1 | 8/2018 | Lang et al. |
| 2019/0216472 A1 | 7/2019 | Shah |

\* cited by examiner

Table I

| Implant Size | Maximum A/P Distance Measured (mm) |
|---|---|
| 3 | 44 - 46.5 |
| 4 | 46.5 - 49.5 |
| 5 | 49.5 - 52.5 |
| 6 | 52.5 - 55.5 |
| 7 | 55.5 - 58.5 |
| 8 | 58.5 - 61.5 |
| 9 | 61.5 - 64.5 |
| 10 | 64.5 - 67.5 |

*FIG. 5A*

Table II

| Implant Size | Surface Area Measured Across Medial Condyle (mm$^2$) |
|---|---|
| 3 | 722.5 |
| 4 | 808.2 |
| 5 | 921.3 |
| 6 | 999 |
| 7 | 1204.8 |
| 8 | 1434 |

FIG. 5B

Table III

| Implant Size | Maximum M/L Distance Measured (mm) |
|---|---|
| 1 | 54.1 |
| 3N | 56.8 |
| 2 | 57.2 |
| 4N | 59.9 |
| 3 | 60.3 |
| 5N | 63 |
| 4 | 63.4 |
| 6N | 66.1 |
| 5 | 66.5 |
| 6 | 69.6 |
| 7 | 72.7 |
| 8 | 75.8 |
| 9 | 78.9 |
| 10 | 82 |

SYSTEMS AND METHODS FOR SELECTING ARTIFICIAL FEMORAL COMPONENTS

PRIORITY CLAIM

This application is a continuation-in-part of copending U.S. patent application Ser. No. 16/392,282, filed Apr. 23, 2019, which is hereby incorporated herein by reference in its entirety.

BACKGROUND OF THE INVENTION

Field of the Invention

The present technology relates generally to systems and methods for selecting and implanting artificial femoral components.

Related Art

The present invention relates generally to systems and methods such as those utilized in techniques known as Total Knee Replacement (or Total Knee Arthroplasty, "TKA"). During a TKA procedure, load-bearing parts of the knee joint are replaced with artificial prostheses.

The femoral component of the TKA procedure is a rounded implant, mimicking the natural shape of the joint. To prepare the femur for the implant, the distal end of the femur is resected into a generally flat plane. After resection, a complex mechanism has been used to measure the anteroposterior (A/P) size of the femur to determine the proper size of the femoral implant component. This conventional device is not only very cumbersome, it typically requires access to the anterior cortex of the femur located proximally further along the surface of the femur. This requires an undesirably large incision and possibly traumatic retraction of the muscle for visualization, which necessarily increases the complexity and risk of the surgery. This large incision is also cosmetically unpleasant. The large incision and complex measuring structure also contribute significantly to the duration of the procedure.

SUMMARY OF THE INVENTION

In accordance with one aspect of the technology, a method of determining a size of a femoral component to be implanted in a patient is provided. The method can include creating an axial cut surface extending across a medial condyle of a patient's femur. A distance across the axial cut surface across the medial condyle can be measured. A femoral component can be selected based on the distance measured.

In accordance with another aspect of the invention, an assembly is provided for preparing a femur to receive an implant. The assembly can include an A/P chamfer cutting block positionable on an axial cut surface of the femur to provide a guide for producing anterior and posterior and chamfer cuts on the femur. At least one rotational guide can be coupled to the A/P chamfer cutting block. At least a portion of the at least one rotational guide can be positionable on a posterior surface of at least one of the medial condyle or lateral condyle of the patient's femur to thereby rotationally orient the A/P chamfer cutting block relative to the patient's femur.

In accordance with another aspect of the technology, a rotational guide assembly is provided for orienting a cutting block relative to a patient's femur. The assembly can include a base support having a front face and a rear face. The rear face can be configured to be mounted upon a chamfer cutting block mountable upon an axial cut surface formed through a patient's femur. At least one alignment foot can extend from the base support. The alignment foot can be oriented to contact at least one of the posterior surface of the medial condyle or the lateral condyle of the patient's femur when the A/P chamfer cutting block is mounted to the axial cut surface of the patient's femur. At least one opening can be formed through the base support, the opening being alignable with an opening formed in the chamfer cutting block to provide a line of sight through the base support and the chamfer cutting block to the axial cut surface of the patient's femur.

In accordance with another aspect of the technology, a system is provided for preparing a femur to receive an implant. The system can include a saw blade, positionable in a first saw blade slot of a distal femoral cutting block and being operable to resect the femur to form an axial cut surface thereon. The saw blade can carry nominal A/P sizing indicia on a first side thereof and can carry nominal M/L sizing indicia on a second, opposite side thereof. The saw blade can be positionable across the axial cut surface in a first orientation to compare the nominal A/P sizing indicia to an anteroposterior dimension of the medial condyle and can be positionable across the axial cut surface in a second orientation to compare the nominal M/L sizing indicia to a mediolateral dimension of the medial condyle.

BRIEF DESCRIPTION OF THE DRAWINGS

The following drawings illustrate exemplary embodiments for carrying out the invention. Like reference numerals refer to like parts in different views or embodiments of the present invention in the drawings.

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Definitions

As used herein, the singular forms "a" and "the" can include plural referents unless the context clearly dictates otherwise. Thus, for example, reference to "indicia" can, if the context so dictates, include one or more sets or collections of signs, symbols, markings, etc.

As used herein, the term "substantially" refers to the complete or nearly complete extent or degree of an action, characteristic, property, state, structure, item, or result. As an arbitrary example, an object that is "substantially" enclosed is an article that is either completely enclosed or nearly completely enclosed. The exact allowable degree of deviation from absolute completeness may in some cases depend upon the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. As another arbitrary example, a composition that is "substantially free of" an ingredient or element may still actually contain such item so long as there is no measurable effect as a result thereof.

As used herein, the term "about" is used to provide flexibility to a numerical range endpoint by providing that a given value may be "a little above" or "a little below" the endpoint.

Relative directional terms can sometimes be used herein to describe and claim various components of the present invention. Such terms include, without limitation, "distal," "proximal," "anterior," "posterior," "upward," "downward," "horizontal," "vertical," etc. These terms are generally not intended to be limiting, but are used to most clearly describe and claim the various features of the invention. Where such terms must carry some limitation, they are intended to be limited to usage commonly known and understood by those of ordinary skill in the art in the context of this disclosure. In some instances, dimensional information is included in the figures. This information is intended to be exemplary only, and not limiting. In some cases, the drawings are not to scale and such dimensional information may not be accurately translated throughout the figures.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Invention

The present technology relates generally to techniques and apparatus for implanting femoral components as part of a partial or full knee replacement surgery. Such techniques are useful, for example, in Total Knee Replacement (or Total Knee Arthroplasty, "TKA"). During a TKA procedure, load-bearing parts of the knee joint are replaced with artificial prostheses. Typical TKA procedures can involve substantial postoperative pain and can require weeks of physical rehabilitation. The surgical incision necessary for such procedures can extend for several inches above and below the patella.

The femoral component of the TKA procedure is a rounded implant, mimicking the natural shape of the bone. To prepare the femur for the implant, the distal end of the femur is resected into a generally flat plane. After resection, a complex mechanism has conventionally been used to measure the anteroposterior ("A/P") size of the femur to determine the proper size of the femoral implant component. In some cases, a second mechanism has also been used to measure the mediolateral ("M/L") size of the femur. One such conventional device to measure the A/P size of the femur is shown, for example, in U.S. Pat. No. 9,681,963, to Leslie et al. This measuring instrument is not only very cumbersome, it typically requires access to the anterior cortex of the femur located proximally further along the surface of the femur. This requires an undesirably large incision which necessarily increases the complexity and risk of the surgery, with muscle retraction further adding risk of injury to the soft tissue. This large incision is also cosmetically unpleasant. The large incision and complex measuring structure also contribute significantly to the duration of the procedure.

The present inventor has developed techniques and instruments that significantly decrease the size of the incision required for such surgery, and also reduce the complexity of the implant component determination. The present inventor has found that her system can decrease the total surgery time by as many as twelve minutes. This decrease in surgery time is accomplished while also significantly reducing the size of incision required. Reducing the cumbersome prior art apparatuses from the instrumentation tray also allows significant reduction in the number of trays required to perform the procedure. Thus, the present apparatuses and techniques reduce surgical time, costs, risks and postoperative recovery time associated with total knee replacements. As the surgical incision required is also much smaller, the postoperative scarring is more cosmetically acceptable.

Implantation of femoral components is generally accomplished by creating an incision in the patient's knee to expose the ends of the femur and the tibia. Typically, a parapatellar approach is utilized, with the patella then being displaced to one side of the joint. This allows exposure of the distal end of the femur and the proximal end of the tibia. These ends are then very accurately cut and shaped to receive implant components.

While those of ordinary skill in the art will readily appreciate the surgical techniques necessary to implant femoral components, to simplify the discussion herein, the figures illustrate, sometimes partially, a human femur in isolation. This is done with the understanding that such will generally never be the case in actual practice.

Figure 1:
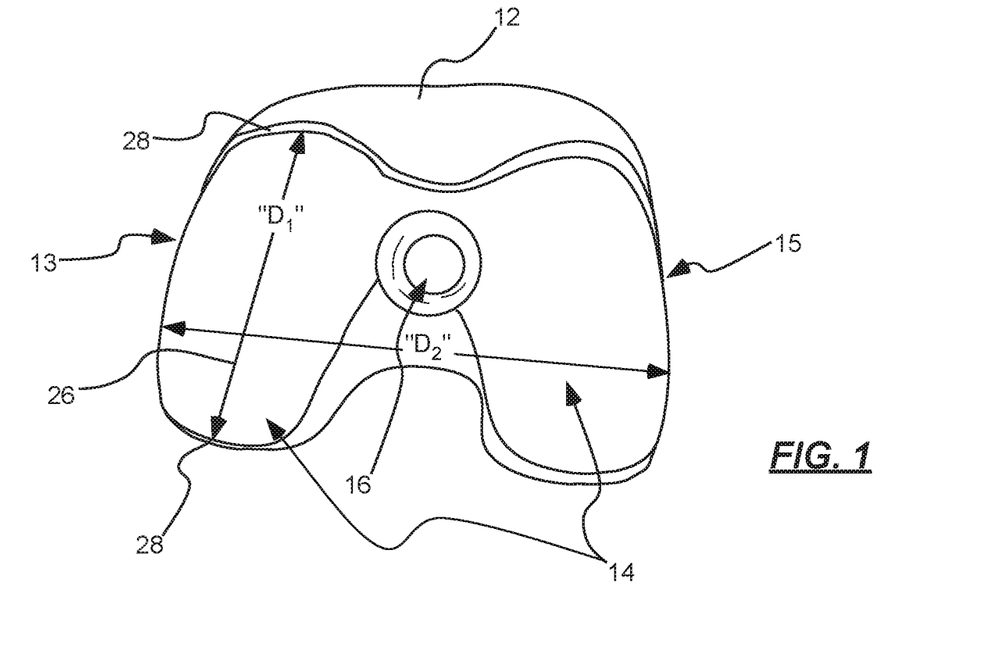
FIG. 1 is an end view of a human femur having an axial cut surface formed thereon.
Figure 2:
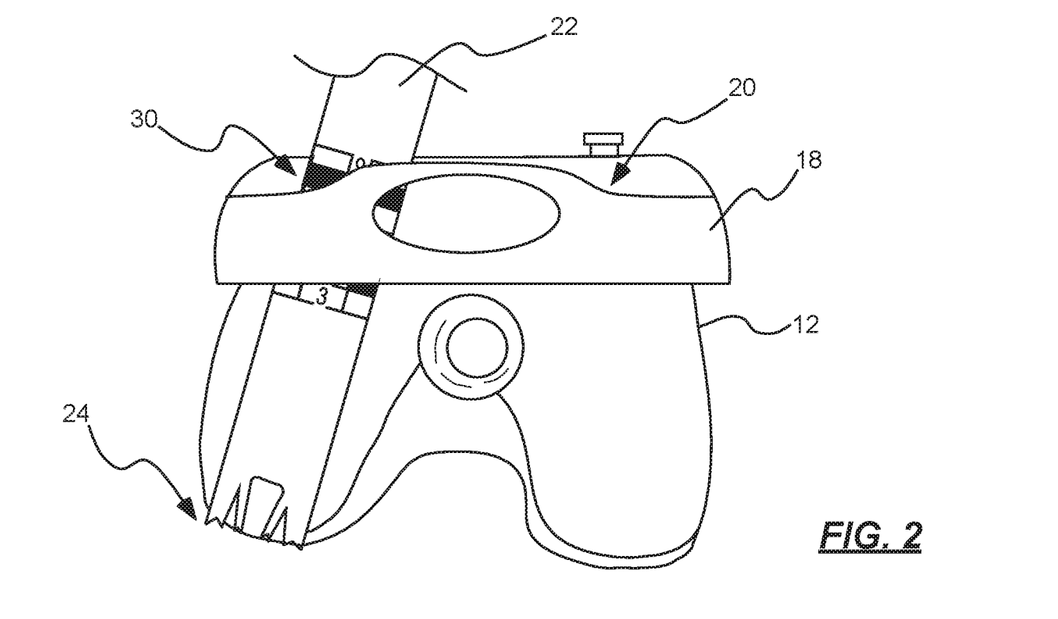
FIG. 2 is an end view of the femur of FIG. 1 with a distal femoral cutting block positioned thereon, with a saw blade inserted into the distal femoral cutting block.

Turning now to FIGS. 1 and 2, a human femur 12 is shown having had already formed thereon an axial cut surface 14. Formation of the axial cut surface can be accomplished in a number of ways. Oftentimes, an intramedullary hole or canal 16 is created in the femur to receive a rod of a resection jig (not shown). This jig can allow a distal cutting block (18 in FIG. 2) to be precisely pinned to the femur. The distal cutting block can include one or more saw blade slots 20 formed therein for receiving a saw blade 22. The saw blade shown is a sagittal saw blade with cutting teeth formed on a distal end 24 thereof. The cutting teeth and general configuration of the saw blade shown are exemplary only: a variety of differing configurations can be utilized. In addition to the sagittal blade shown, a variety of other suitable blades can be used, such as oscillating or reciprocating saw blades and the like. Other techniques for removing or shaping bone can also be used, such as laser or ultrasonic saws.

The saw blade 22 is shown fully extended through the femur in FIG. 2, after the saw blade has formed the axial cut surface 14 (FIG. 1) on the femur. Generally, the saw blade is extended through the saw blade slot 20 and is coupled to a saw (on a proximal end, not shown, opposite that of end 24) that drives the saw blade in an oscillatory or other motion. As the saw blade is advanced through the saw blade slot, it removes bone and creates the axial cut surface shown. Generally speaking, after the axial cut surface is formed, the distal cutting block 18 can be removed.

The depth of the distal femoral (axial) cut is manufacturer specific and generally depends on the thickness of the metal for their specific implant. Most manufacturers have a 9 mm distal femoral cut with some at 8 mm. These are only exemplary measurements for one of the most commonly used manufacturers. The consistent methodology of the present technology allows for projectional calculations according to resected depth and manufacturer-specific sizing.

The distal femoral cut is measured by a distal femoral cutting block which is laid against the outermost portion of the medial condyle positioning the cutting slot at 9 mm from that surface. The surgeon can modify this spot as needed in case of a local defect to arrive at the 9 mm distal femoral cut, as their training dictates their interpretation of anatomic anomaly.

Figure 7:
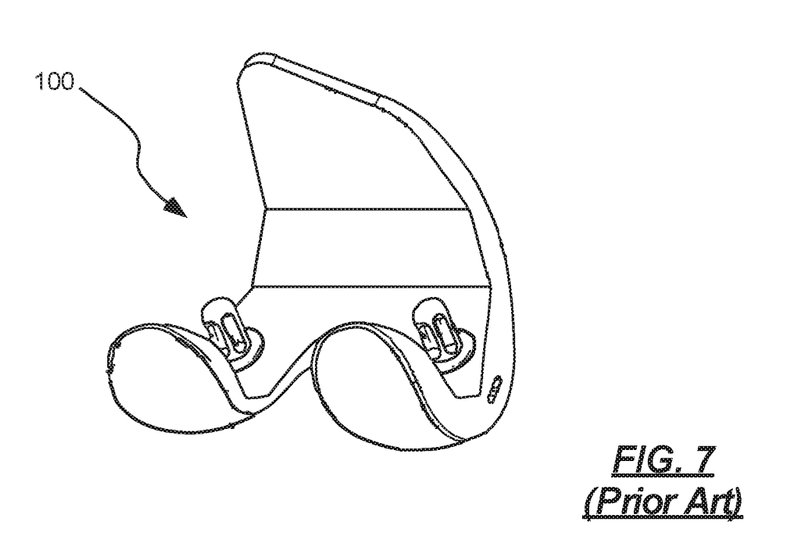
FIG. 7 is a perspective view of an exemplary PRIOR ART femoral implant component.

Once the axial cut surface 14 is formed on the distal end of the femur 12, the present system provides a manner by which a femoral implant component can be selected. An exemplary femoral implant similar to those found in the prior art is shown by example at 100 in FIG. 7. As the various sizes of such implant components vary between patients, selecting the proper size for any particular patient has been challenging and has to date required very sophisticated equipment and time-consuming techniques.

The present inventor, however, has developed a system by which the proper implant component can be relatively easily selected. As shown in FIG. 1, at least a portion of the axial cut surface 14 has been formed to extend through the medial condyle 13 (the lateral condyle is shown on the right at 15). A distance 26, shown by example at dimension $D_1$ can be measured across the medial condyle to determine the antero-posterior dimension of the femur. Based, in some embodiments, solely upon this measurement, the proper size of femoral component can be selected for the particular femur. The distance 26 can be measured in a variety of locations, but in some embodiments is selected to be taken across the maximum dimension of the medial condyle across the axial cut surface.

In the example shown, the maximum distance $D_1$ is shown extending from one surface of the bone to another surface of the bone. Generally speaking, after resection of the femur (e.g., after formation of the axial cut surface across the femur), cartilage 28 may remain on the femur around the axial cut surface. Depending upon the measurement device utilized, and the manner in which the distance is measured, the maximum distance may be measured from anterior bone surface to posterior bone surface, as shown, or may be measured from outer surface to outer surface of the cartilage 28. The measurement can also be made from bone surface to cartilage surface or cartilage surface to bone surface, etc.

Figure 3A:
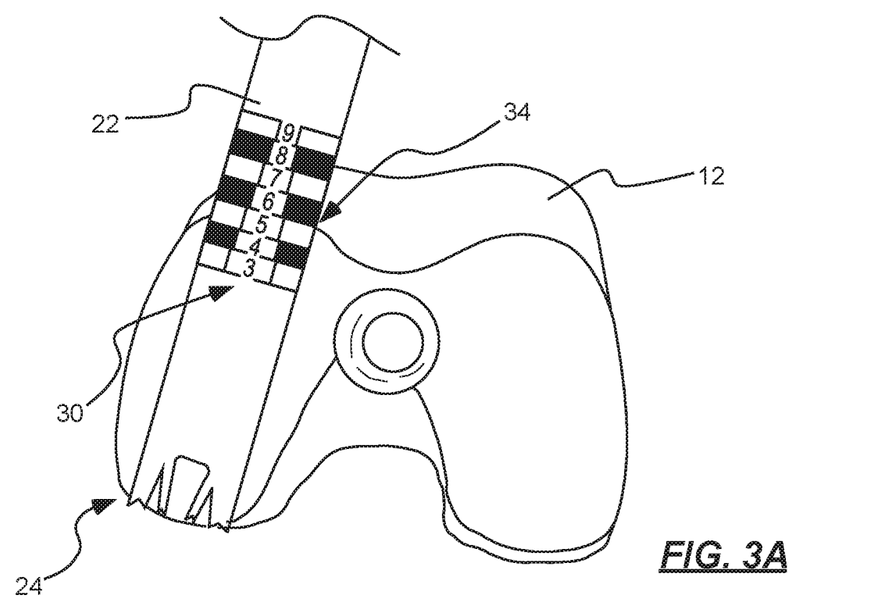
FIG. 3A is an end view of the femur of FIG. 1 with a saw blade carrying nominal A/P sizing indicia positioned thereon.
Figure 3B:
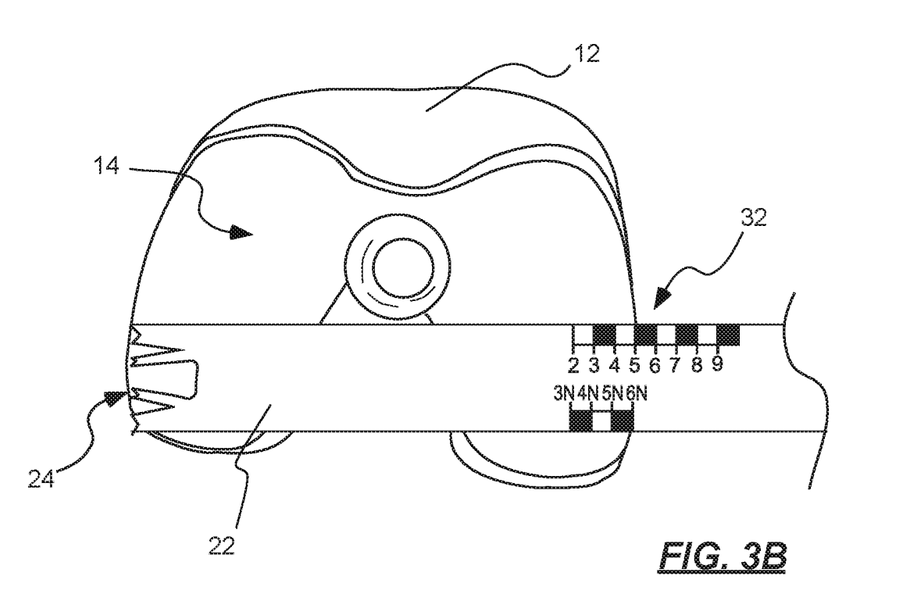
FIG. 3B is an end view of the femur of FIG. 1 with a saw blade carrying M/L nominal sizing indicia positioned thereon.

In one aspect of the invention, the maximum distance can be measured by using indicia carried by the saw blade 22. This aspect of the invention is shown in more detail in FIGS. 3A, 3B, 8A and 8B. As shown in FIG. 3A, in one aspect of the technology, the maximum distance is measured using nominal A/P sizing indicia 30 carried by the saw blade 22. The nominal A/P sizing indicia 30 can omit any actual physical dimensional data and can be correlated to nominal sizes of femoral components. In the example shown, the nominal sizing indicia indicates that a size 5 implant is required for the size of the femur 12 shown, as indicated by reference numeral 34.

Figure 5A:
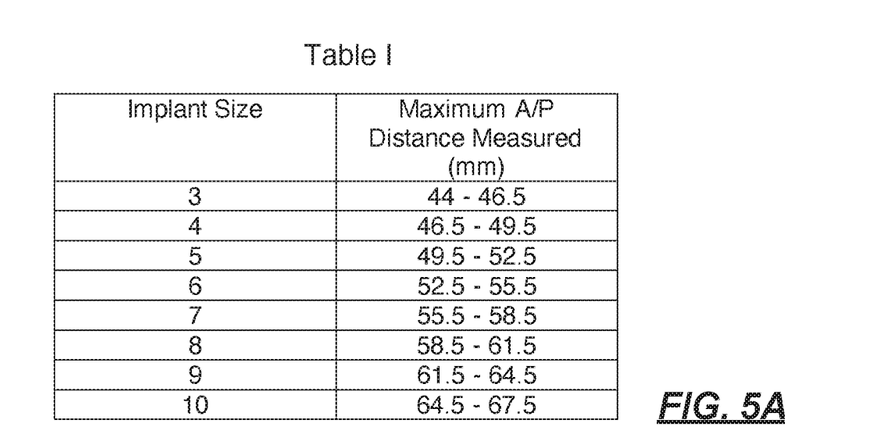
FIG. 5A is a table showing correlating data relevant to exemplary nominal sizing indicia associated with maximum A/P dimension.

Generally speaking, the nominal A/P sizing indicia 30 can be correlated to a particular manufacturer's implant system before applying the indicia to the saw blade 22. In this manner, a specific saw blade, having nominal sizing indicia specific to any given manufacturer, can be used for each of a number of implant component systems. Table I in FIG. 5A provides an exemplary data chart that can be used, for example, to correlate the nominal sizing to an actual dimension across the axial cut surface. This table is provided for its exemplary teaching only: the nominal sizing indicia will generally have to be tailored to each specific manufacturer.

In the examples shown, the nominal A/P sizing indicia 30 carried by the saw blade 12 increments negatively from an anterior top of concavity of the medial condyle to a posterior top of concavity of the medial condyle, when the saw blade is positioned on the axial cut surface of the patient's femur. In other words, the indicia increments positively from the posterior top of concavity of the medial condyle to the anterior top of concavity. In this manner, the surgeon or technician can align the distal end of the saw blade with the top of concavity of the posterior condyle of the medial condyle, as shown in FIG. 3A, and read the correct nominal size from the indicia at the anterior top of concavity.

In another aspect of the technology, the distance $D_1$ (FIG. 1) (or the distance $D_2$, or an area 27 of the axial cut surface, discussed in more detail below) can be measured by reviewing an image taken of the axial cut surface 14. Suitable imaging techniques can include, without limitation, CT, MRI, radiographic and other imaging or photographic modalities. The type of imaging technique utilized may also dictate which surfaces are used to measure the distance, as some imaging techniques do not capture the cartilage 28. In another aspect, the axial cut surface can be taken virtually: that is, the femur need not be cut to predict the femoral component applicable to the present patient. In this embodiment, a CT scan, or other suitable imaging technology, can virtually create the axial cut surface without requiring any incisions be formed in the patient. Once such an image is obtained, the distance $D_1$ or $D_2$ or area 27 can be measured using suitable technology.

By utilizing imaging technology to measure actual features of the medial condyle, the present system can be used to predict the femoral implant size for any particular patient before the patient undergoes surgery. Imaging can be done prior to surgery to further decrease surgical time and complexity.

Figure 4:
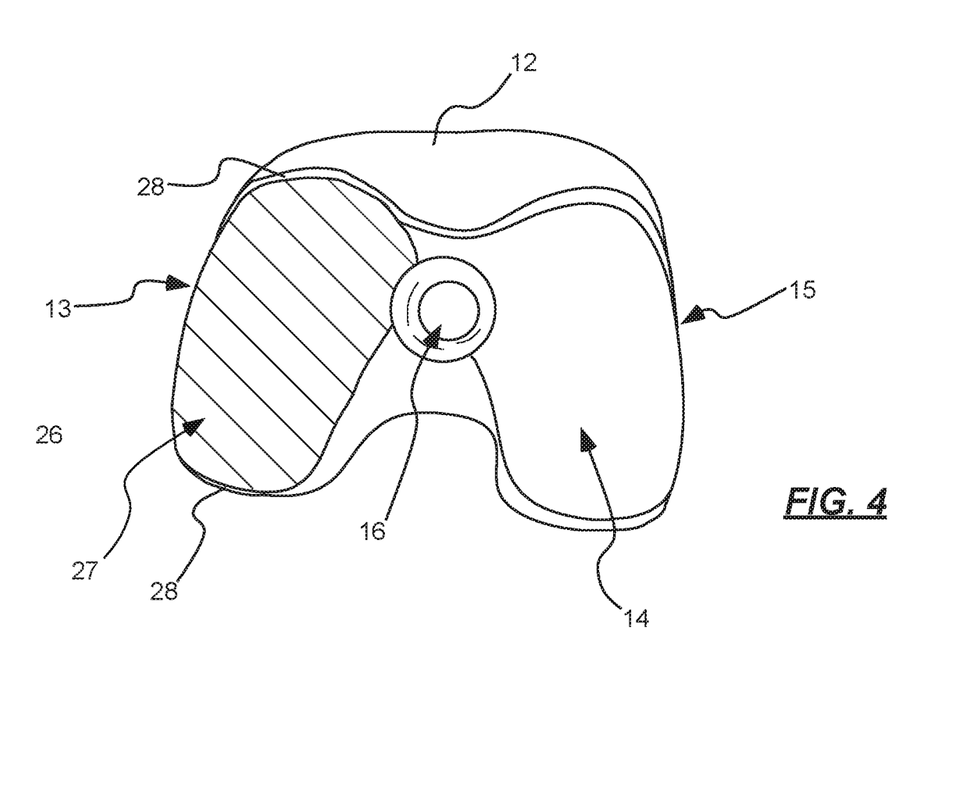
FIG. 4 is an end view of the femur of FIG. 1 with an exemplary area calculation zone illustrated thereon.
Figure 5B:
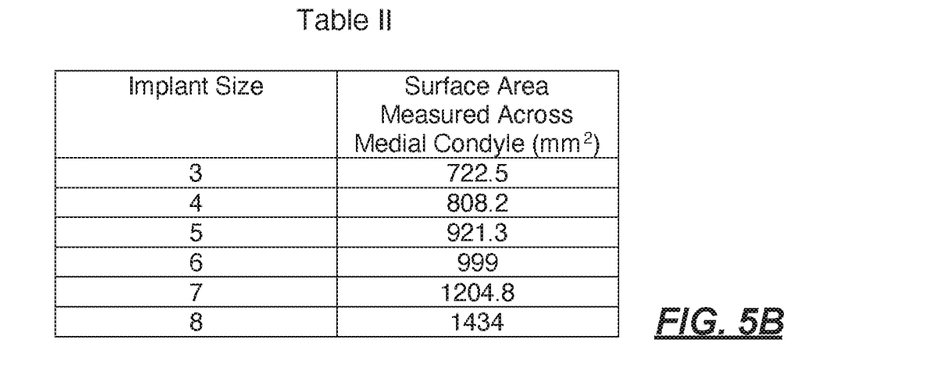
FIG. 5B is a table showing correlating data relevant to exemplary nominal sizing indicia associated with an area of the medial condyle across the axial cut.

In addition to using either of the two methods above to obtain a plane across the medial condyle to measure the distance $D_1$ across the medial condyle, the present technology can use a variety of dimensional data relative to the medial condyle to predict the size of a femoral component for a particular patient. In the example shown in FIG. 4, the area 27 of the plane (physical or virtual) formed across the medial condyle can be used to select the size of the femoral implant. Table II, FIG. 5B, illustrates exemplary implant sizes correlated with surface areas of exemplary medial condyles.

Figure 5C:
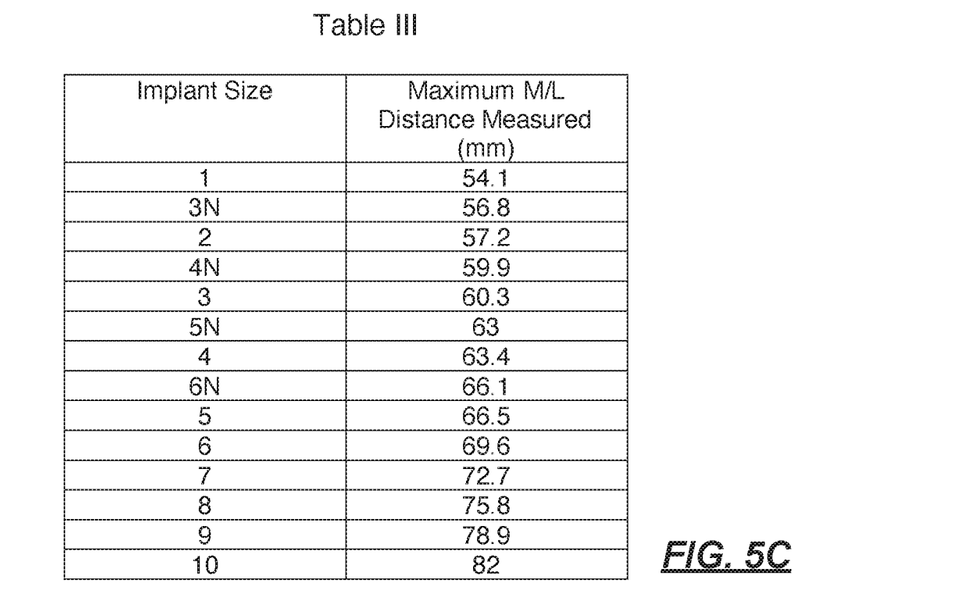
FIG. 5C is a table showing correlating data relevant to exemplary nominal sizing indicia associated with maximum M/L dimension.
Figure 8A:
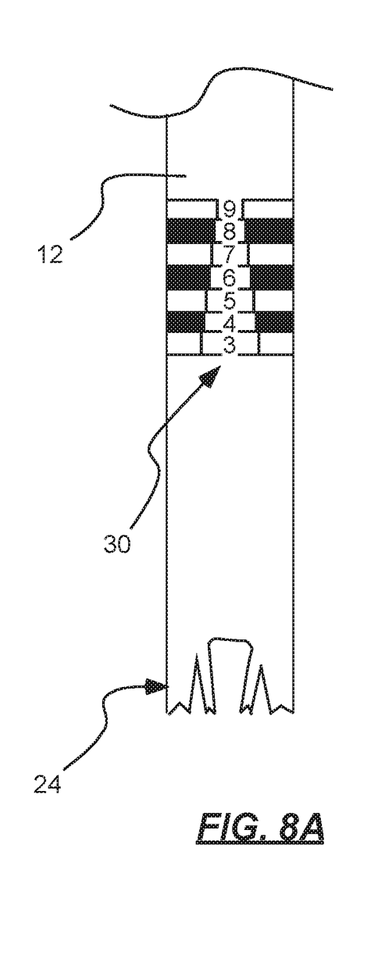
FIG. 8A is a front view of a saw blade carrying nominal A/P sizing indicia on a front face thereof.
Figure 8B:
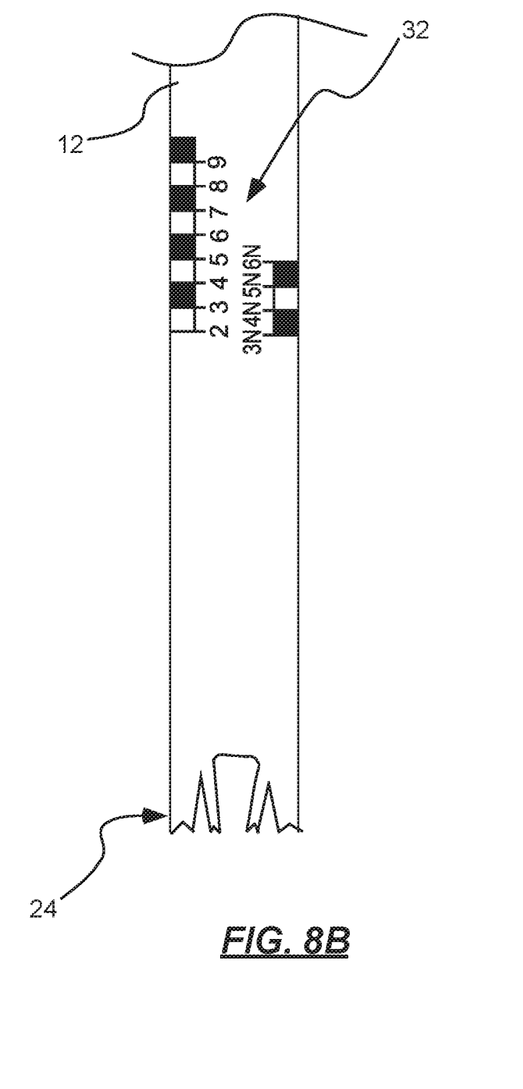
FIG. 8B is a rear view of the saw blade of FIG. 8A, showing nominal M/L sizing indicia carried on a rear side thereof.

As shown in FIGS. 8A and 8B, in one aspect of the invention, the nominal A/P sizing indicia 30 can be carried on a first side of the saw blade (FIG. 8A) and nominal M/L sizing indicia 32 can be carried by a second, opposite side of the saw blade (FIG. 8B). Table III, FIG. 5C, illustrates exemplary implant sizes correlated with M/L dimensions of exemplary medial condyles. The nominal M/L sizing indicia can be used to measure the mediolateral dimension, $D_2$ in FIG. 1, of the axial cut surface. This can further increase accuracy of the implant selection and aid in correctly fitting a wider variety of patients with anatomic variations. In most cases, measuring the mediolateral dimension of the axial cut surface across the femur and measuring the anteroposterior dimension of the lateral condyle will indicate the same implant size. In some cases, however, measuring the M/L dimension will indicate a slightly different implant size is required for a particular patient, referred to as A/P vs. M/L mismatch. The present technology allows a surgeon to very quickly gain an indication of this mismatch, as it will be indicated by the difference in sizing of the A/P and M/L dimension. This can greatly aid a surgeon in quickly deciding which implant size is best for any particular patient, or whether additional surgical maneuvers should be done to reposition the A/P chamfer cutting block at the beginning of the procedure. In many conventional cases, the surgeon would otherwise be required to recut the surfaces at the end of the procedure, the point in time at which the mismatch is most often discovered using prior art technology.

Thus, the saw blade 12 can include two configurations: a first configuration in which the saw blade extends across the anteroposterior dimension of the medial condyle, and second configuration in which the saw blade is turned to expose the second side of the blade and extends across the mediolateral dimension of the axial cut surface.

In addition to using the saw blade 22 discussed above to obtain the A/P or M/L dimension, an alternate device (not shown) that carries the nominal A/P and M/L indicia can be used. For example, the nominal A/P or M/L indicia can be applied to a segment of suitable material such as plastic, metal, etc. This can be positioned as referenced above and used to obtain the A/P or M/L dimension quickly and effectively.

Figure 6:
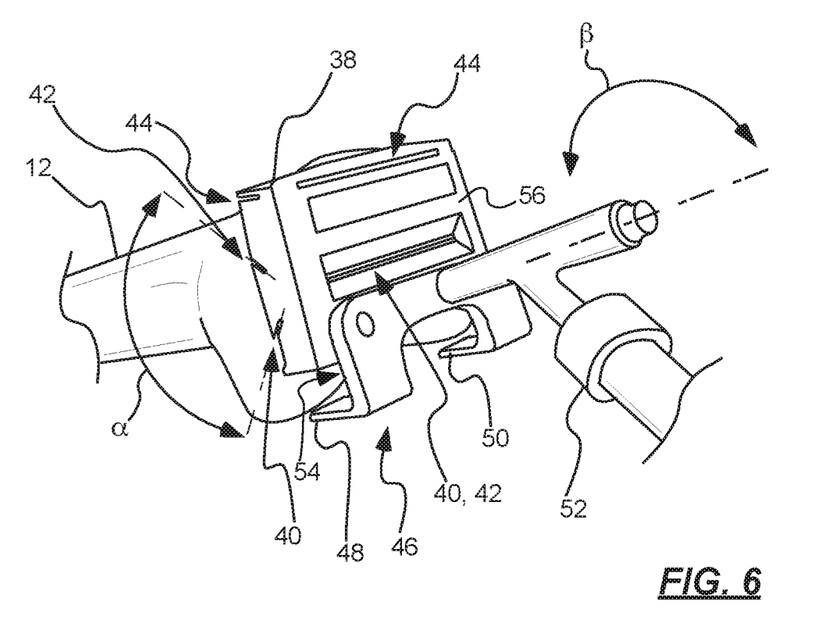
FIG. 6 is a perspective view the femur of FIG. 1 with an A/P chamfer cutting block and rotational guide positioned thereon.
Figure 10A:
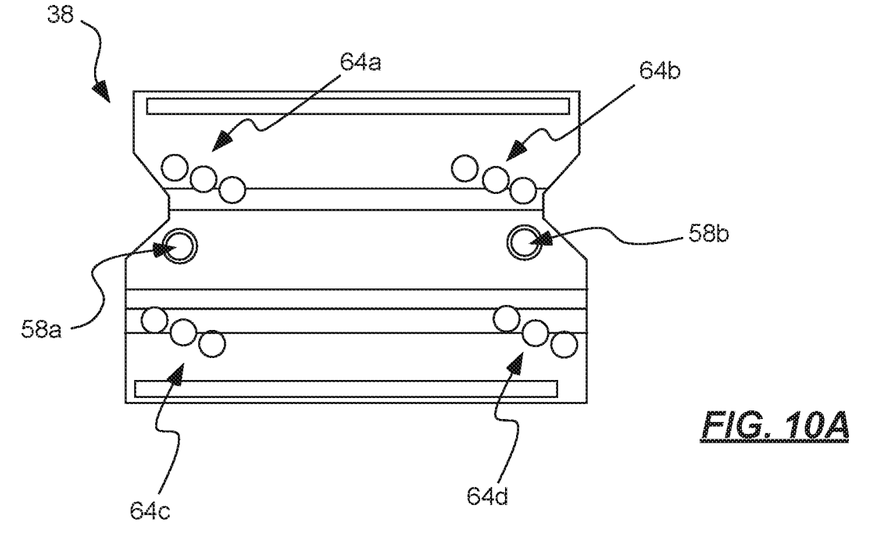
FIG. 10A is a rear view an exemplary A/P chamfer cutting block in accordance with the present technology.
Figure 10B:
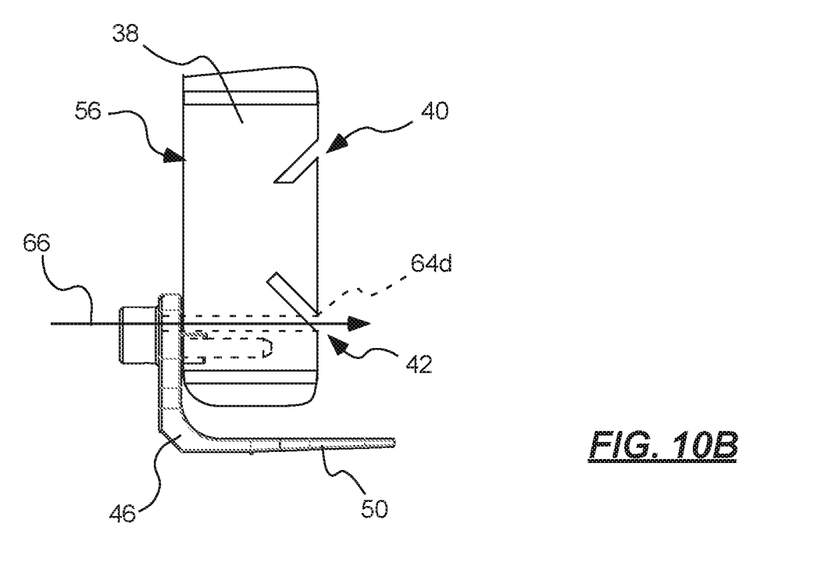
FIG. 10B is a side view of the A/P chamfer cutting block of FIG. 10A, shown with the rotation guide of FIG. 9A attached thereto.

As shown in FIGS. 6, 10A and 10B, in one aspect of the invention an A/P chamfer cutting block 38 can be provided. The chamfer cutting block illustrated in the figures is provided for reference only. Various manufacturers provide such cutting blocks with varying features positioned in varying locations on the cutting blocks. The A/P chamfer cutting block can be aligned relative to and fixed to the axial cut surface 14 (FIG. 1) in a number of manners known to those of ordinary skill in the art. For example, once properly positioned, the chamfer cutting block can be pinned to the axial cut surface via anchoring pins inserted through openings 58a, 58b shown in FIG. 10A. The A/P chamfer cutting block can include one or more saw blade slots or guides 40, 42, etc. The saw blade slots can be operable to receive a saw blade to aid in forming chamfer or condyle cuts in the femur to shape the femur to receive the implant component. The chamfer saw blade slots can be angled relative to one another at angle shown of "α" (FIG. 6). The angle α can vary, depending upon the implant system being used, but is generally between about 0 degrees and about 180 degrees.

In the embodiment shown, the A/P chamfer cutting block 38 can include or can carry or can be coupled to at least one rotational guide 46 (FIGS. 6, 9A-9D and 10B). In one embodiment, the A/P chamfer cutting block is attached directly to the rotational guide and the two are installed on the axial cut surface as an assembled pair. The rotational guide can include a rear face 54 and the chamfer cutting block can include a front face 56. The rear face of the rotational guide and the front face of the chamfer cutting block can be mated directly to one another to form an assembled unit.

The rotational guide can include a pair of alignment feet or tabs 48, 50, which can extend generally perpendicularly to the rear face 54 of the rotational guide. These tabs can be placed on the posterior condyle of at least one of the medial condyle or the lateral condyle to thereby rotationally orient the A/P chamfer cutting block relative to the femur. The rotational guide of 3 degrees external rotation to the posterior condylar axis would align the A/P chamfer block along the epicondylar axis. A separate 5 degree external rotational guide can be used for knees with valgus deformity. The rotational guide, once affixed to the A/P chamfer cutting block, can be used to place the cutting block in the correct orientation parallel to the epicondylar axis as is the standard of treatment. The A/P cutting block then can be securely fixed to the femur and allow cuts to proceed uninterrupted without needing to remove any additional pins, where such have been used by previous systems.

Appropriate positioning and orientation of the A/P chamfer cutting block on the femur allows accurate cuts and hence accurate affixing of the femoral component onto those cuts. Thus the described rotational guide is used to appropriately align the femoral component along the epicondular axis to allow proper mechanical tracking of the patella and biomechanical functioning of the endoprosthetic knee. A handle 52 can be fixed to the rotational guide to aid in positioning the rotational guide (and hence the A/P chamfer cutting block) relative to the femur.

The rotational guide 46 is shown in more detail in FIGS. 9A through 9D. The guide can include a base support 60 that can exhibit the front face 46 and the rear face 54. In the example shown, two alignment feet 48, 50 can extend from the base support, each oriented to contact a posterior surface of one of the medial condyle or the lateral condyle of the patient's femur when the chamfer cutting block is mounted to the axial cut surface of the patient's femur. At least one opening 62a, 62b can be formed through the base support. The opening can be alignable with an opening (for example, one of several sets of openings 64a, 64b, 64c, 64d in FIG. 10A) formed in the chamfer cutting block 38. This aspect of the technology can provide a line of sight, shown for example at 66 in FIGS. 9D and 10B through the base support and the chamfer cutting block to the axial cut surface of the patient's femur. In this manner, the surgeon can either visually check the placement of the assembly on the axial cut surface, or use a pin or laser or similar device, to ensure that the chamfer cutting block is properly positioned on the surface. The surgeon is then able to move the A/P chamfer block anterior or posterior with affixed orientation to improve the fit with A/P-M/L mismatch.

The rotational guide can include a handle attachment interface 53 that can aid in attaching handle 52 (FIG. 6). Opposite the handle attachment interface, an anchor device or pin 68 can extend from the rear face of the base support 60. The anchoring device or pin 68 can be fitted, for example, in an opening in the chamfer cutting block to provide a first anchoring point between the rotational guide and the A/P chamfer cutting block to increase rotational stability of the coupling between the rotational guide and the AP chamfer cutting block. In addition, second and third anchoring pins 70a, 70b, respectively, can also be fixed to or extend from the rear face of the base support. The second and third anchoring pins can be fitted within one of the sets of openings 64a-64d of the cutting block 38 shown in FIG. 10A. Collectively, the anchoring pins can provide at least a two but more effectively three or more anchoring point interfaces between the rotational guide and the A/P chamfer cutting block. This can ensure that the rotational guide is securely attached to the chamfer cutting block to ensure the two do not rotate or slip relative to one another.

Figures 9A, 9B, 9C, 9D:
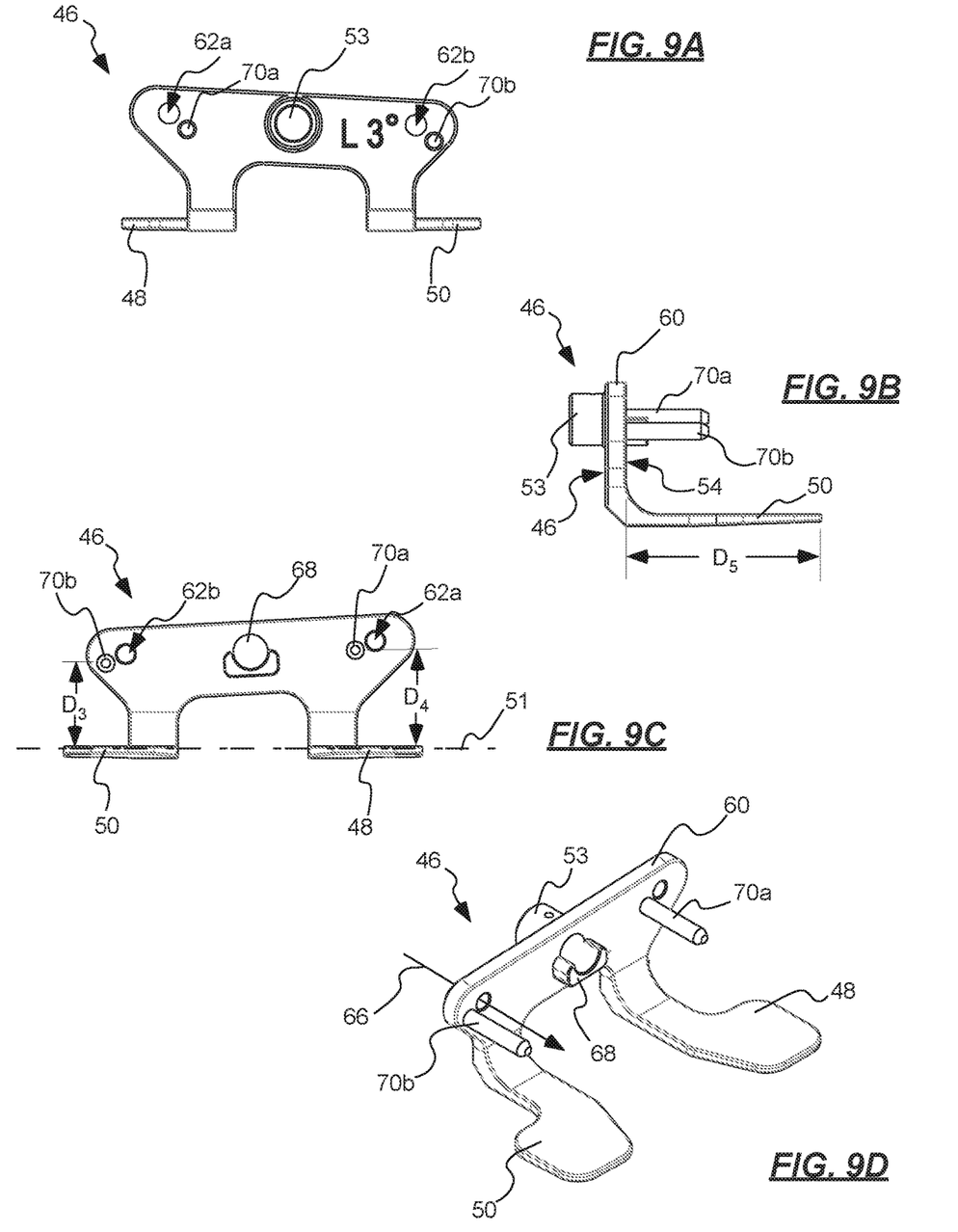
FIG. 9A is a front view of an exemplary rotation guide in accordance with an embodiment of the technology.
FIG. 9B is a side view of the rotation guide of FIG. 9A.
FIG. 9C is a rear view of the rotation guide of FIG. 9A.
FIG. 9D is a perspective view of the rotation guide of FIG. 9A.

Generally, the two alignment feet 48, 50 are aligned on a plane, shown at 51 in FIG. 9C. To achieve the rotation desired, the anchoring pins 70a, 70 can be offset relative to this plane. In other words, pin 70a can be displaced from plane 51 by distance $D_4$ and pin 70b can be displaced by distance $D_3$. In this example, distance $D_3$ is less than distance $D_4$, which results in the two being vertically offset relative to one another. While these dimensions can vary, in one embodiment, $D_3$ is about 0.603 inches and $D_4$ is about 0.698 inches, resulting in a rotation of about 3 degrees. These dimensions can vary, however, depending upon the rotation that is desired. For example, for a 5 degree rotation, $D_4$ can be greater, on the order of about 0.761 inches.

As the openings 62a, 62b in the rotational guide are similarly aligned with one of the openings 64a-64d in the chamfer cutting block, they are also offset vertically relative to one another. Thus, when the surgeon fits anchoring pins 70a, 70b within one of the sets of openings 64a-64d, another of the openings cooperates with openings 62a, 62b in the rotational guide to provide the line of sight 66 shown in FIG. 10B.

As shown in FIG. 9B, the alignment feet or tabs 48, 50 generally extend perpendicularly from the rear face 54 of the base support 60 for a distance $D_5$. This distance is generally great enough to ensure that the alignment feet extend far enough beyond the chamfer cutting block 38 to engage the posterior surfaces of the condyles of the femur once the cutting block and rotational guide assembly are attached to the femur. While this distance can vary for differing chamfer cutting blocks, in one example this distance is between about 1 inch and about 2 inches. In one example, the distance is between about 1.25 inches and 1.75 inches. In one example, the distance $D_5$ is about 1.568 inches.

Utilizing the present technology, a surgeon or technician can relatively easily determine the proper orientation of the A/P chamfer block allowing direct pinning of the block to the bone without the need for exchange guide pins or alternative fixation methods, which are used with conventional systems. In these prior art systems, the orientation is fixed early in the procedure with pins that allow placement of the A/P chamfer block on the pins, to only be removed later on to allow the cuts through the cutting block to proceed. This is cumbersome, and increases the complexity of the case, as pins can be placed erroneously, or move between passing of the instruments resulting in error, injury to the surgeon or assistants or the patient. These conventional systems also unnecessarily complicate and lengthen the procedure. With the present technology, the procedure is more precise and shorter.

While these fixed rotations of the present rotational guides can vary, in one embodiment, they are selected from either a 3 degree rotation or a 5 degree rotation and can be provided for right- or left-sided implantations. The A/P chamfer cutting block can then be properly aligned on the axial cut surface prior to forming any chamfer or condyle cuts.

In addition to the structural components described above, the present technology also provides methods of determining the proper size of a femoral implant component, methods of preparing a distal end of a femur for implantation. In one particular example, the technology provides a method of determining a size of a femoral component to be implanted in a patient. In this example, a distal cutting block can be positioned on a distal end of a patient's femur, the distal cutting block having a first saw blade slot associated therewith. A saw blade can be positioned in the first saw blade slot to form an axial cut surface on the distal end of the patient's femur, at least a portion of the axial cut surface extending through the medial condyle. A maximum distance of the axial cut surface across the medial condyle can be measured. A femoral component can be selected based on the maximum distance measured. In one example, the femoral component can be selected based solely on the maximum distance measured.

Measuring the maximum distance can include measuring using nominal sizing indicia carried by the saw blade used to form the axial cut surface. The nominal sizing indicia carried by the saw blade can increment negatively from an anterior top of concavity of the medial condyle to a posterior top of concavity of the medial condyle, when the saw blade is positioned on the axial cut surface of the patient's femur. The nominal sizing indicia can be carried by the saw blade and can include incremental indicia correlating to nominal femoral components. Measuring the maximum distance can include measuring using an image of the axial cut surface.

Selecting a femoral component can include comparing the maximum distance measured to a set of femoral implants having varying nominal sizes. The method can include positioning an A/P chamfer cutting block on the axial cut surface, the A/P chamfer cutting block carrying at least one rotational guide, and positioning the at least one rotational guide on a posterior surface of at least one of the medial condyle or the lateral condyle to thereby rotationally orient the A/P chamfer cutting block. The one or more rotational guides can be attached to the A/P chamfer cutting block at a fixed orientation based on the axial cut surface.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

I claim:

1. An assembly for preparing a femur to receive an implant, the assembly comprising: an A/P chamfer cutting block positionable on an axial cut surface of the femur to provide a guide for producing chamfer cuts on the femur, the A/P chamfer cutting block having a front face opposite a face positionable on the axial cut surface of the femur; the NP chamfer cutting block including at least two saw blade slots, the at least two saw blade slots being angled relative to one another at an angle, one of the saw blade slots angling upwardly from the front face of the NP chamfer cutting block and another of the saw blade slots angling downwardly from the front face of the A/P chamfer cutting block, the at least two saw blade slots operable to each receive a saw blade therein to allow formation of chamfer cuts in the femur when the NP chamfer cutting block is positioned on the axial cut surface of the femur: and a rotational guide assembly coupled to the A/P chamfer cutting block, at least a portion of the a rotational guide assembly positionable on a posterior surface of at least one of the medial condyle or lateral condyle of the patient's femur to thereby rotationally orient the NP chamfer cutting block relative to the patient's femur while the chamfer cuts are performed.

2. The assembly of claim 1, wherein the rotational guide assembly includes a base support having a rear face: the front face of the A/P chamfer cutting block mating with the rear face of the base support of the rotational guide assembly.

3. The assembly of claim 1, wherein the rotational guide assembly includes at least one alignment foot, the alignment foot extending rearwardly from the rotational guide assembly and beyond the A/P chamfer cutting block so as to be capable of contacting a posterior surface of at least one of the medial condyle or the lateral condyle of the patient's femur when the A/P chamfer cutting block is attached on the axial cut surface of the patient's femur.

4. The assembly of claim 1, wherein the rotational guide assembly includes a base support, and further comprising at least one opening formed through the base support and at least one opening formed through the A/P chamfer cutting block, the openings being aligned with one another when the base support of the rotational guide assembly is coupled to the A/P chamfer cutting block so as to provide a line of sight through each to the axial cut surface of the patient's femur.

5. The assembly of claim 4, further comprising a handle attached to the base support and extending from the front face of the base support, the handle being graspable by a user to allow the user to manipulate the chamfer cutting block when the rotational guide is attached to the chamfer cutting block.

6. The assembly of claim 4, further comprising a first anchoring pin extending from the rear face of the base support, the first anchoring pin providing an anchoring attachment to the A/P chamfer cutting block.

7. The assembly of claim 6, further comprising:
second and third anchoring pins extending from the rear face of the base support, the second and third anchoring pins providing second and third anchoring points, respectively, between the rotational guide and the chamfer cutting block.

8. An assembly for preparing a femur to receive an implant, the assembly comprising: an A/P chamfer cutting block positionable on an axial cut surface of the femur to provide a guide for producing chamfer cuts on the femur, the A/P chamfer cutting block having a front face opposite a face positionable on the axial cut surface of the femur; the NP chamfer cutting block including at least two saw blade slots, the at least two saw blade slots being angled relative to one another at an angle, one of the saw blade slots angling upwardly from the front face of the A/P chamfer cutting block and another of the saw blade slots angling downwardly from the front face of the A/P chamfer cutting block, the at least two saw blade slots operable to each receive a saw blade therein to allow formation of chamfer cuts in the femur when the A/P chamfer cutting block is positioned on the axial cut surface of the femur; and a rotational guide assembly coupled to the A/P chamfer cutting block, the rotational guide assembly including: a base support having a rear face matable with the front face of the A/P chamfer cutting block mating; and at least one alignment foot; the at least one alignment foot extending rearwardly from the rotational guide assembly and beyond the A/P chamfer cutting block so as to be capable of contacting a posterior surface of at least one of the medial condyle or the lateral condyle of the patient's femur when the A/P chamfer cutting block is attached on the axial cut surface of the patient's femur to thereby rotationally orient the A/P chamfer cutting block relative to the patient's femur while the chamfer cuts are performed.

9. The assembly of claim 8, further comprising a handle attached to the base support and extending from the front face of the base support, the handle being graspable by a user to allow the user to manipulate the chamfer cutting block when the rotational guide is attached to the chamfer cutting block.

10. The assembly of claim 8, further comprising a first anchoring pin extending from the rear face of the base support, the first anchoring pin providing an anchoring attachment to the A/P chamfer cutting block.

11. The assembly of claim 10, further comprising:
second and third anchoring pins extending from the rear face of the base support, the second and third anchoring pins providing second and third anchoring points, respectively, between the rotational guide and the chamfer cutting block.

* * * * *

UNITED STATES PATENT AND TRADEMARK OFFICE
CERTIFICATE OF CORRECTION

| | |
|---|---|
| PATENT NO. | : 11,819,423 B2 |
| APPLICATION NO. | : 16/856776 |
| DATED | : November 21, 2023 |
| INVENTOR(S) | : Anna Andranik Kulidjian |

It is certified that error appears in the above-identified patent and that said Letters Patent is hereby corrected as shown below:

In the Claims

Column 11, Line 30, delete "NP" and insert --A/P--

Column 11, Line 33, delete "NP" and insert --A/P--

Column 11, Line 38, delete "NP" and insert --A/P--

Column 11, Line 44, delete "NP" and insert --A/P--

Column 12, Line 25, delete "NP" and insert --A/P--

Signed and Sealed this
Twenty-third Day of April, 2024

Katherine Kelly Vidal
*Director of the United States Patent and Trademark Office*